US011660017B2

(12) United States Patent
Greiser

(10) Patent No.: US 11,660,017 B2
(45) Date of Patent: May 30, 2023

(54) MEDICAL DATA ACQUISITION

(71) Applicant: Siemens Healthcare GmbH, Erlangen (DE)

(72) Inventor: Andreas Greiser, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 192 days.

(21) Appl. No.: 17/105,270

(22) Filed: Nov. 25, 2020

(65) Prior Publication Data

US 2021/0153766 A1 May 27, 2021

(30) Foreign Application Priority Data

Nov. 27, 2019 (EP) .................................... 19211886

(51) Int. Cl.
*A61B 5/055* (2006.01)
*G01R 33/34* (2006.01)

(52) U.S. Cl.
CPC .......... *A61B 5/055* (2013.01); *G01R 33/3403* (2013.01); *A61B 2562/182* (2013.01)

(58) Field of Classification Search
CPC ................ A61B 5/055; G01R 33/3403; G01R 2562/182
See application file for complete search history.

(56) References Cited

U.S. PATENT DOCUMENTS

| 4,668,915 A | 5/1987 | Daubin et al. | |
|---|---|---|---|
| 6,198,283 B1* | 3/2001 | Foo | G01R 33/561 324/309 |
| 6,298,112 B1* | 10/2001 | Acharya | G06T 11/005 378/4 |
| 6,325,540 B1* | 12/2001 | Lounsberry | A61B 8/565 378/114 |
| 6,351,122 B1* | 2/2002 | Polzin | G01R 33/561 324/309 |
| 6,353,445 B1* | 3/2002 | Babula | G16H 40/67 715/733 |
| 6,359,961 B1* | 3/2002 | Aufrichtig | A61B 6/548 378/98.2 |
| 6,362,620 B1* | 3/2002 | Debbins | G01R 33/54 324/309 |
| 6,377,162 B1* | 4/2002 | Delestienne | G16Z 99/00 340/286.07 |
| 6,379,306 B1* | 4/2002 | Washburn | G01S 7/52071 600/454 |
| 6,381,557 B1* | 4/2002 | Babula | G16H 40/40 702/183 |

(Continued)

FOREIGN PATENT DOCUMENTS

WO 2015047273 A1 4/2015

OTHER PUBLICATIONS

Search Report dated Jul. 22, 2020 for European Patent Application No. 19211886.7.

*Primary Examiner* — Dixomara Vargas
(74) *Attorney, Agent, or Firm* — Banner & Witcoff Ltd.

(57) ABSTRACT

A system for medical data acquisition comprising a plurality of scanners and a plurality of infrastructure units to operate the scanners, wherein the system is designed to use at least one of the infrastructure units as a common infrastructure unit to operate at least two of the scanners. Also, a method to control this system.

13 Claims, 3 Drawing Sheets

(56) References Cited

U.S. PATENT DOCUMENTS

| | | | | |
|---|---|---|---|---|
| 6,408,043 B1* | 6/2002 | Hu | A61B 6/541 | 378/20 |
| 6,412,980 B1* | 7/2002 | Lounsberry | A61B 6/581 | 378/114 |
| 6,442,290 B1* | 8/2002 | Ellis | H04N 1/04 | 711/200 |
| 6,483,933 B1* | 11/2002 | Shi | A61B 6/581 | 382/132 |
| 6,494,831 B1* | 12/2002 | Koritzinsky | G16H 40/40 | 128/903 |
| 6,500,122 B1* | 12/2002 | Washburn | G01S 7/52073 | 600/443 |
| 6,501,818 B1* | 12/2002 | Ali | G01N 23/046 | 378/4 |
| 6,501,849 B1* | 12/2002 | Gupta | G16H 30/20 | 382/152 |
| 6,546,230 B1* | 4/2003 | Allison | G09B 7/00 | 434/350 |
| 6,574,518 B1* | 6/2003 | Lounsberry | A61B 8/56 | 378/207 |
| 6,578,002 B1* | 6/2003 | Derzay | G16H 40/40 | 705/2 |
| 6,581,069 B1* | 6/2003 | Robinson | G16H 40/67 | 707/648 |
| 6,598,011 B1* | 7/2003 | Howards | G16H 40/67 | 382/141 |
| 6,609,217 B1* | 8/2003 | Bonissone | G16H 40/40 | 714/26 |
| 6,691,134 B1* | 2/2004 | Babula | A61B 8/565 | |
| 7,263,710 B1* | 8/2007 | Hummel, Jr. | G16H 40/40 | 434/323 |
| 7,774,211 B1* | 8/2010 | Mullen | G06Q 10/10 | 705/2 |
| 9,331,772 B2* | 5/2016 | Harris, III | H04B 7/082 | |
| 2001/0018659 A1* | 8/2001 | Koritzinsky | G16H 30/40 | 705/3 |
| 2002/0004798 A1* | 1/2002 | Babula | G16H 40/63 | |
| 2002/0063560 A1* | 5/2002 | Debbins | G01R 33/54 | 324/309 |
| 2003/0014425 A1* | 1/2003 | Accardi | G16H 40/40 | |
| 2003/0061071 A1* | 3/2003 | Babula | G16H 50/20 | 705/2 |
| 2003/0181804 A1* | 9/2003 | Gagnon | G16H 15/00 | 600/410 |
| 2006/0101836 A1 | 5/2006 | Tanaka | | |
| 2006/0195564 A1* | 8/2006 | Accardi | G16H 40/20 | 709/223 |
| 2007/0004980 A1* | 1/2007 | Warner | G01S 7/52017 | 600/411 |
| 2007/0124169 A1* | 5/2007 | Irving | G16H 30/40 | 382/128 |
| 2011/0081065 A1 | 4/2011 | Canstein | | |
| 2011/0121969 A1* | 5/2011 | Mercer | G08B 21/185 | 340/540 |
| 2011/0166440 A1 | 7/2011 | Harvey | | |
| 2011/0302414 A1* | 12/2011 | Logan | G16H 80/00 | 713/168 |
| 2014/0029818 A1* | 1/2014 | McCoy | G06T 11/003 | 382/131 |
| 2014/0278496 A1 | 9/2014 | Spencer | | |
| 2015/0142462 A1* | 5/2015 | Vaidya | G16H 40/63 | 705/2 |
| 2015/0153428 A1 | 6/2015 | Chen | | |
| 2016/0227676 A1 | 8/2016 | Zhou et al. | | |
| 2017/0231508 A1* | 8/2017 | Edwards | A61M 16/021 | 600/301 |
| 2018/0146919 A1* | 5/2018 | Abrams | G06Q 10/06 | |
| 2019/0108902 A1* | 4/2019 | Parthan | G16H 30/20 | |
| 2019/0369180 A1* | 12/2019 | Chang | G01R 33/443 | |
| 2020/0168324 A1* | 5/2020 | Parthan | G16H 40/20 | |
| 2021/0192727 A1* | 6/2021 | Ward | G06V 10/82 | |
| 2022/0137172 A1* | 5/2022 | Speckner | G01R 33/5611 | 324/309 |

* cited by examiner

FIG 1
(Conventional)
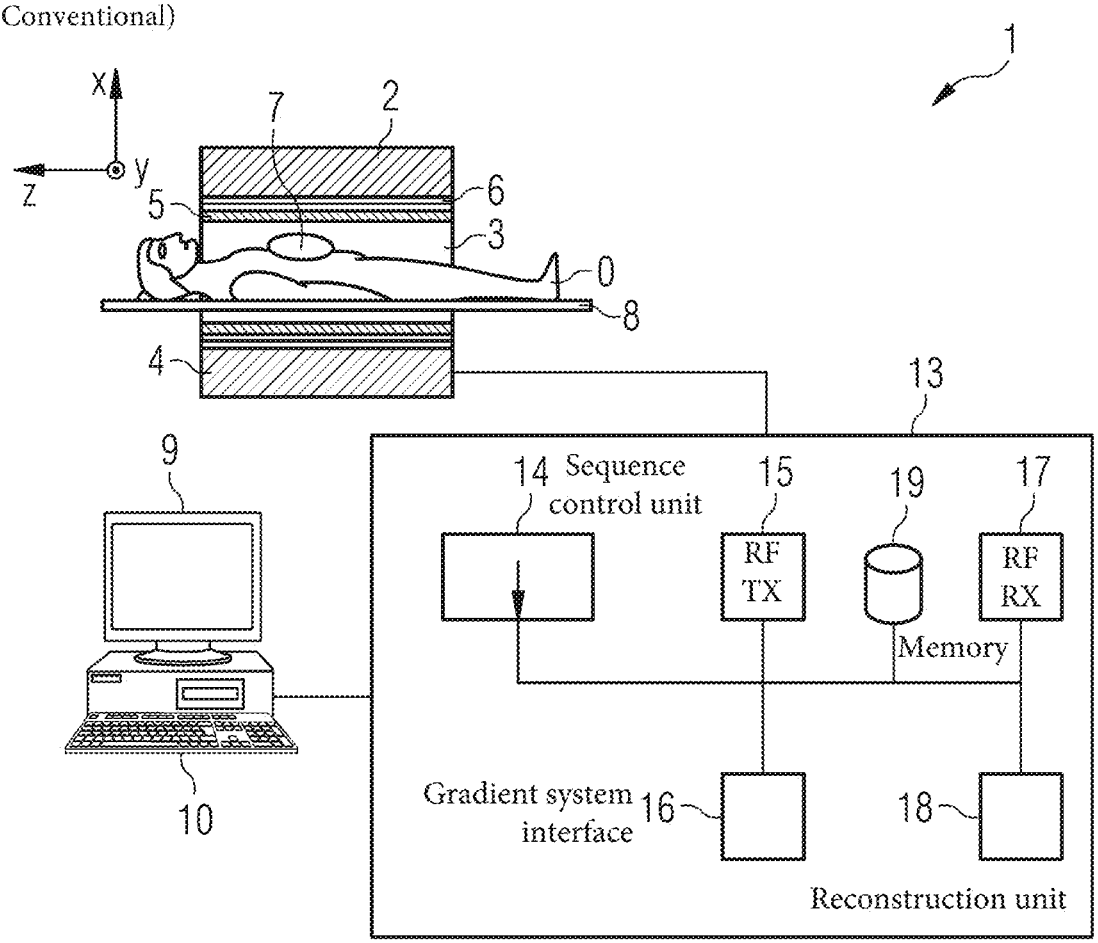

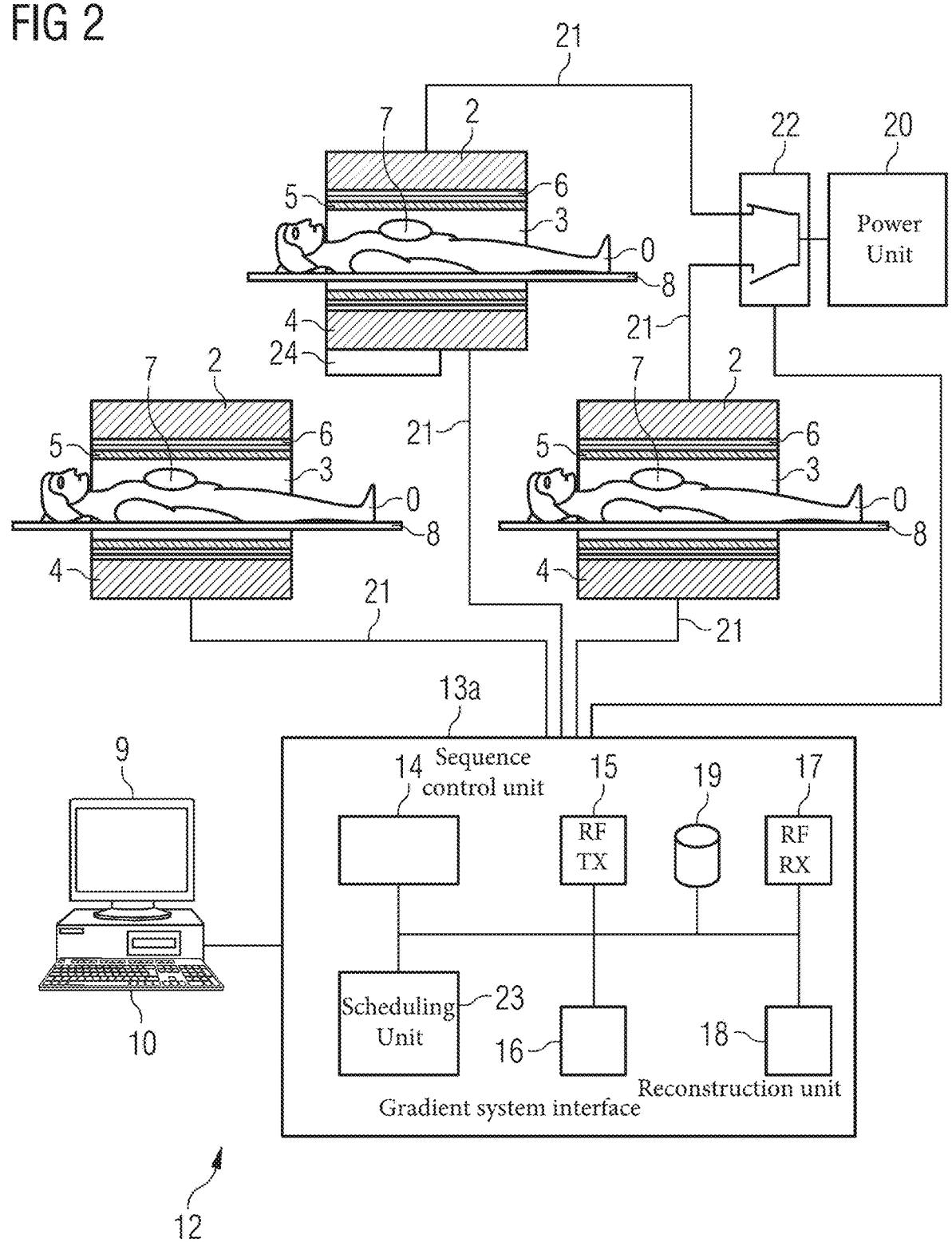

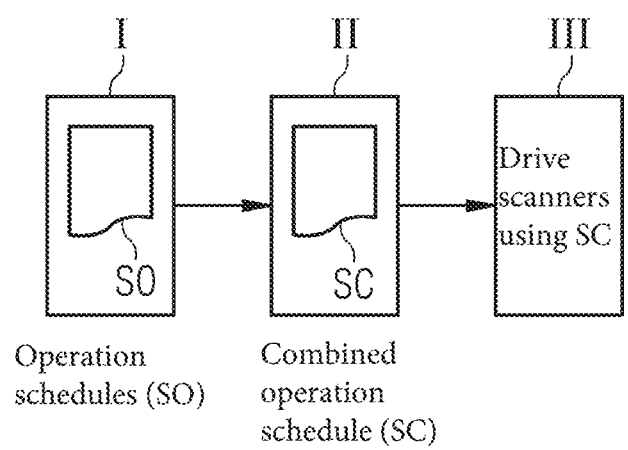

MEDICAL DATA ACQUISITION

TECHNICAL FIELD

The disclosure describes a system for medical data acquisition, especially for medical image acquisition systems, as well as a method to control such system.

BACKGROUND

The acquisition of medical data is necessary for modern medicine. Besides "simple" acquisition like measuring temperature or blood pressure, there are more complex data measured with medical examination devices, which are often medical image acquisition devices like e.g. magnetic resonance imaging ("MRI") devices or computer-tomography ("CT") devices. Typically these devices are closed stand-alone devices which are an arrangement of units closely working together.

For example, a magnetic resonance imaging apparatus includes the actual magnetic resonance scanner in which a patient or test person is positioned on a driven bed. The magnetic resonance scanner is typically equipped with a basic field magnet system, a gradient system as well as an RF transmission antenna system and an RF reception antenna system. At least the basic field magnet system (and especially also the gradient system) typically comprises auxiliary units like cooling units, power units like power amplifiers and sensor units. Furthermore, the MRI apparatus has a central control device that is used to control the MRI apparatus. This central control device typically includes a sequence control unit for measurement sequence control, a radio-frequency transmission device that generates and amplifies RF pulses, a gradient system interface, a radio-frequency reception device and a reconstruction unit that receives the acquired raw data and reconstructs magnetic resonance image data therefrom for the measurements.

Up to now all MR scanners, but also all other medical examination devices are installed as independent, self-contained units. This is advantageous in the case only one device is used, e.g. in a private doctor's surgery. However, this is a financial and systematic (space, energy and infrastructure) disadvantage in the case a whole "fleet" of, especially similar, examination devices is used as in a hospital, since every single examination device is delivered with all of its components.

SUMMARY

It is the object of the present disclosure to improve the known devices and methods to facilitate an improvement in medical data acquisition, especially in medical image acquisition.

A system according to the disclosure for medical data acquisition comprises two or more scanner units and a number of infrastructure units for the operation of the scanner units, wherein the system is designed such that it is able to use an infrastructure unit as a common infrastructure unit for the operation of at least two of the scanner units.

With "system" there is not meant a common apparatus for medical data acquisition, e.g. one single MRT-apparatus, but a plurality of such devices arranged in connection with another, e.g. as a "fleet" of devices. The disclosure is especially advantageous in the case there are individual scanner units of the same type, e.g. two or more MRT-devices or two or more CT-devices, since these could be run in a common network allowing a good distribution of resources. However, the scanner units may also be of different types. Although the disclosure is applicable for all possible data acquisition devices, it is very advantageous for image acquisition devices, since these devices are typically very complex and need a vast number of different (expensive) units to work properly.

According to the disclosure it is necessary that the system comprises two or more scanner units. As "scanner units" all units are meant that are able to examine (scan) a patient in order to acquire medical data. In the following scanner units are also designated simply as "scanners". The disclosure is very advantageous for image-scanners, e.g. MRT-scanners or CT-scanners, since these devices need a vast number of different units to work properly, such as e.g. cooling units, auxiliary systems and power units. Regarding the system according to the disclosure, one can say that the scanners are bundled into one "multi-scanning facility".

These different units are designated here and in the following as "infrastructure units", since they provide the infrastructure for a scanner to scan properly. One could say that the infrastructure units deliver the "infrastructure medium" for the scanners. This infrastructure medium does not necessarily have to be a physical fluid, but can be also energy or a data stream. Some exemplary infrastructure units (with the according infrastructure medium in parentheses) are—auxiliary units, such as a cooling unit (cooling medium), a sensor unit (data stream, measurement voltage or measurement current) or a unit providing energy for auxiliary systems (energy), power units (energy, electromagnetic waves), preferably a general power supply or a power amplifier, e.g. for RF or gradients in MRI, computing units (data stream), preferably an image reconstruction unit or an analysis unit and control units (data stream, control voltage or control current), preferably comprising a user interface.

shielding/insulation units like Faraday cage or acoustic damping insulation

In contrast to the state of the art, where every device has its own infrastructure units, the system according to the disclosure is designed such that it is able to use an infrastructure unit as a common infrastructure unit for the operation of at least two of the scanners. This means that it is not necessary in every possible case that a common infrastructure unit (the unit designed to drive two scanners at the same time) is hardwired to two or more scanners (although this also enclosed in the meaning of "able to use"), however it is necessary that the system can connect at least one single infrastructure unit to two or more scanners. Thus, the disclosure comprises systems where two or more scanners are hardwired to at least one infrastructure unit as well as systems comprising switches to connect an infrastructure unit with two or more scanners.

It should be noted that an "infrastructure unit" is an infrastructure unit typically included in a common medical examination device and not a power plant nor the power grid of a hospital nor the Ethernet of a hospital. One could preferably say that an infrastructure unit is a unit designed to directly be connected with a scanner. One could also say that an infrastructure unit is a unit designed to directly provide a scanner with a respective infrastructure medium.

It is preferred that the infrastructure medium of the common infrastructure device is no data stream, especially no data stream of acquired data, wherein it is not excluded that such data stream is running in addition to the infrastructure medium in the system. It is preferred that an infrastructure unit provides an infrastructure medium for operating a scanner. Particularly preferred common infrastructure units are units providing a cooling or heating medium and power units.

The disclosure is especially advantageous in the course of scanner setups where multiple scan volume instances are provided by design. Just as the B0 field generating unit is capable of providing multiple scans simultaneously by sharing the same B0 field, the other infrastructure needs can be shared across the scan places of the system.

A method according to the disclosure for controlling a system comprises the following steps:

Providing or determining an operation schedule for the operation of at least two scanner units. The operation schedule is a dataset of operation data of any of the scanners. It comprises information about scheduled operation times and preferably also operation about the need of an infrastructure medium (especially of (all) needed infrastructure media. It could be provided, e.g. as a list, by a user or read from a memory. It could also be determined from operation datasets or datasets provided by medical examining apparatuses or schedules.

Determining a combined operation schedule of combined operation of the at least two scanner units with a concerted use of a common infrastructure unit based on the schedule for the operation of the at least two scanner units and technical properties of the common infrastructure unit. This does not necessarily involve an operation of the scanners at the same time (however, this aspect is a special advantage of the disclosure). In every case comprises the combined operation schedule an operation of two scanners by the same common infrastructure unit (at the same time or interleaved).

Operating the at least two scanner units, especially interleaved or combined with the common infrastructure unit at least temporally, according to the determined combined operation schedule.

For example, two scanners need cooling and power and the first scanner should run from 9 am to 10:30 am and the second scanner should run from 10 am to 11 am. Then the combined operation schedule could easily schedule the cooling and power for 9 to 11 with a cooling/power connection for both scanners at the scheduled operation times. In the case, the cooling is sufficient for the two scanners, but the technical properties of the power unit are not sufficient to drive both scanners at the same time (wherein a sufficient power output for at least two scanners is actually preferred), then the combined operation schedule could either shift the operation time for the second scanner from 10:30 to 11:30 or each scanner can use its own power unit or at the time from 10 to 10:30 another power unit is aiding the (first) power unit.

A (managed) performance scheduling device according to the disclosure for a system according to the disclosure, is designed to perform a method according to the disclosure. It preferably comprises the following components:

a data interface design to read and/or determine an operation schedule for the operation of at least two scanner units, a determination unit designed for determining a combined operation schedule of combined operation of the at least two scanner units with a concerted use of a common infrastructure unit based on the operation schedule for the operation of the at least two scanner units and technical properties of the common infrastructure unit, and an operating unit, designed for operating the at least two scanner units according to the determined combined operation schedule. This operating unit could be a data interface designed to connect to a infrastructure unit, e.g. a control unit of a medical examination apparatus, and sending control data to this infrastructure unit.

Some units or modules of the system or the performance scheduling device mentioned above can be completely or partially realized as software modules running on a processor of a system or a performance scheduling device. A realization largely in the form of software modules can have the advantage that applications already installed on an existing system can be updated, with relatively little effort, to install and run these units of the present application. The object of the disclosure is also achieved by a computer program product with a computer program that is directly loadable into the memory of a device of a system or a performance scheduling device (e.g. of a magnetic resonance imaging apparatus), and which comprises program units to perform the steps of the inventive method when the program is executed by the performance scheduling device or the system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a performance scheduling device or a system. A processor unit can comprise one or more microprocessors or their equivalents.

Features of different claim categories may be combined as appropriate to give further aspects not described herein.

According to a preferred system, an infrastructure unit is a unit selected form the group comprising auxiliary units, preferably a cooling unit, a sensor unit or a unit providing energy for auxiliary systems, power units, preferably a general power supply or a power amplifier, e.g. for RF or gradients in MRI, computing units, preferably an image reconstruction unit or an analysis unit and control units, preferably comprising a user interface.

For example for several MRI scanners, there is especially a common RF- and gradient amplifier power supply and/or a shared cooling water system and/or a shared He-refrigerator and/or a common scan control bus and/or a user interface that can be shared across multiple scan places.

According to a preferred system, the common infrastructure unit is a computing unit designed as a cloud system, especially wherein the cloud system provides capacity for image reconstruction and/or analysis or provides control information for at least two scanner units. Especially preferred is a local cloud setup where the required performance can be allocated on demand.

In a preferred system according to the disclosure, components of the system are part of a data-network, wherein preferably the data-network and scanners (e.g. the magnetic resonance imaging scanners or CT scanners) are in data-communication with each other, wherein the data-network preferably comprises parts of the internet and/or a cloud-based computing system, wherein preferably the system according to the disclosure or a number of components of this system is realized in or controlled by this cloud-based computing system. For example, components of the system, such as a control device or a data reconstruction unit, could be part of a data-network, wherein preferably the data-network and a scanner that is controlled or which provides the image data are in communication with each other. Such a networked solution could be implemented via an internet platform and/or in a cloud-based computing system.

The method may also include elements of "cloud computing". In the technical field of "cloud computing", an IT infrastructure is provided over a data-network, e.g. a storage space or processing power and/or application software. The communication between the user and the "cloud" is achieved by means of data interfaces and/or data transmission protocols.

In the context of "cloud computing", in a preferred aspect of the method according to the disclosure, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred aspect of the system according to the disclosure, the abovementioned units (e.g. the control device, the reconstruction unit, the performance scheduling device) Are present on the "cloud" side. A preferred system further comprises, a local computing unit connected to the system via a data channel (e.g. a data-network, particularly configured as RIS or PACS). The local computing unit includes at least one data receiving interface to receive data. Moreover, it is preferred if the local computer additionally has a transmission interface in order to send data to the system.

A preferred system comprises interlinkage means, preferably power conductors, pipes or data lines, connecting a common infrastructure unit with the scanner units in order to provide the infrastructure medium. A possible infrastructure medium could be energy, cooling medium or data depending on the respective infrastructure unit. Preferably, the system comprises a switch unit designed to connect and disconnect a number of scanner units to/from the common infrastructure unit by connecting or disconnecting interlinkage means. A suitable switch unit could be a controllable electrical switch for power or a controllable valve for a cooling medium. It could also be a router for data.

A preferred system comprises a scheduling unit designed for managing a dynamic connection of the scanner units to a common infrastructure unit in dependence of the maximum and/or optimum performance of said common infrastructure unit. For example, in the case two scanners demand peak performance simultaneously, the temporal alignment may be adopted in an intelligent way in order to avoid high overall peak demands. For example, each measurement may specify the tolerance in the timing for the requested resource, i.e. if in one scan place the RF pulses can be played out interleaved with the RF pulses in another scan place, they can basically share the RF power amplifier.

The temporal alignment may be performed at various timescales. For example, complete scan protocols could be played out in an interleaved manner, because between the scan protocols there may be time needed for breathing commands, playing out adjustments or calibration scans etc., so the interleaving may happen on a seconds timescale. As the atomic elements of MR sequences are played out on a micro-seconds raster, the adaptations may also happen on this timescale, e.g. a gradient pulse is delayed by 100 us in order not start after a gradient pulse is finished in a different unit.

The RF signals could be divided to the scanners via above mentioned switch unit. Preferably, the common infrastructure unit is designed such that it is able to provide a predefined maximum capacity of the respective infrastructure medium (energy, cooling medium, data) required by at least two scanner units.

According to a preferred system, it is designed such that two or more common infrastructure units can be connected to and disconnected from the same scanner units independently, Preferably wherein the system is designed such that a new or additional common infrastructure unit can be additionally connected with scanner units, wherein preferably a common infrastructure unit connected to the scanner units can be disconnected afterwards. This concept enables a continuous renewal of the infrastructure units without any downtimes. For example, first a new unit is added and then the old unit is disconnected.

According to a preferred method, in order to determine the combined operation schedule, the system is initially provided (in a first iteration, in course of the installation) with a proportional scale of infrastructure units to the number of scanner units and then after a time period, the number of infrastructure units in respect to an infrastructure medium is reduced subsequently if the maximum need of the respective infrastructure medium during the time period is covered by a smaller number of respective infrastructure units. Thus, the system can be equipped with a maximum expected resources overshoot and then determined, if infrastructure units can be withdrawn.

Assuming an asynchronous demand for resources, the overall system performance may need to cover a peak demand where the effect of averaging out peak demands is subsequently used to reduce the overall resource requirements. After an analyzing phase the resources may be reduced with this preferred method to a level covering all or a defined cut-off of the observed peak demand.

According to a preferred method, the combined operation schedule is determined based on smart multiplexing and/or interleaving of the usage of infrastructure units for the scanner units. Preferably it is determined, based on the operation schedule of the scanner units, whether the combined performance of the scanner units exceeds the technical properties of the common infrastructure unit at a certain period of time, and in the case of a determined exceedance one of the at least two scanner units are disconnected from the common infrastructure unit and/or another infrastructure unit for the respective infrastructure medium is connected to the scanner units.

Thus, the schedule of combined operation is preferably designed such that the temporal alignment of common infrastructure units and scanners is adopted in an intelligent way in order to avoid high overall peak demands. For example, each measurement may specify the tolerance in the timing for the requested infrastructure medium, e.g. if in one scan place the RF pulses can be played out interleaved with the RF pulses in another scan place, they can basically share the RF power amplifier.

According to a preferred method, the scanner units are driven in a synchronized measurement procedure by a number of common infrastructure units, preferably wherein measurement protocols are scheduled that are similar in regard to the respective infrastructure medium or the time course of the change of the infrastructure medium.

According to a preferred method, the schedule for the operation of at least two scanner units corresponds to a time period longer than a day, especially longer than a month and the determining a schedule of combined operation comprises information about time intervals where the need of the at least two scanner units of the infrastructure medium would exceed the maximum performance of the used common infrastructure unit, wherein a notification for a user is sent or displayed. The notification informs the user that an installation of additional or more powerful respective infrastructure unit will be needed at these time intervals. However, the more intelligence is implemented in the resource scheduling, the less resources are needed overall. Thus, the peak performance can be determined and a suitable number of infrastructure units can be ordered and installed to increase the performance of the system.

According to a preferred method, the system comprises an additional infrastructure unit in addition to the common infrastructure unit that is similar on behalf of the infrastructure medium, wherein the additional infrastructure unit is connected or designed to be connected to an additional scanner unit of the system. Thus, the relative usage of performance can be allocated asymmetrically, i.e. if for some reason there is a need to use one system with higher performance than the other within a cluster of scan places using the same infrastructure. The distribution of resources can be implemented based on priorities, workflows (i.e. allow for more gradient performance in a diffusion scan etc.).

BRIEF DESCRIPTION OF THE DRAWINGS

Other objects and features of the present disclosure will become apparent from the following detailed descriptions considered in conjunction with the accompanying drawings. It is to be understood, however, that the drawings are designed solely for the purposes of illustration and not as a definition of the limits of the disclosure.

FIG. 1 shows a conventional MRI-apparatus.

FIG. 2 shows a simplified system according to an aspect of the disclosure.

FIG. 3 shows a block diagram of the process flow of a preferred method according to the disclosure.

In the diagrams, like numbers refer to like objects throughout. Objects in the diagrams are not necessarily drawn to scale.

DETAILED DESCRIPTION

FIG. 1 shows a schematic representation of a magnetic resonance imaging apparatus 1 ("MRI-apparatus"). The MRI apparatus 1 includes the actual magnetic resonance scanner (data acquisition unit) 2 with an examination space 3 or patient tunnel in which a patient or test person is positioned on a driven bed 8, in whose body the actual examination object is located.

The magnetic resonance scanner 2 is typically equipped with a basic field magnet system 4, a gradient system 6 as well as an RF transmission antenna system 5 and an RF reception antenna system 7. In the shown exemplary aspect, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI apparatus 1 shown here is a whole-body apparatus with a patient tunnel into which a patient can be completely introduced. However, in principle the disclosure can also be used at other MRI apparatuses, for example with a laterally open, C-shaped housing, as well as in smaller magnetic resonance scanners in which only one body part can be positioned.

Furthermore, the MRI apparatus 1 has a central control device 13 that is used to control the MRI apparatus 1. This central control device 13 includes a sequence control unit 14 for measurement sequence control. With this sequence control unit 14, the series of radio-frequency pulses (RF pulses) and gradient pulses can be controlled depending on a selected pulse sequence.

To output the individual RF pulses of a pulse sequence, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI apparatus 1 can thus also be operated by an operator. MR images can also be displayed at the display unit 9, and measurements can be planned and started by means of the input unit (possibly in combination with the display unit 9), and in particular suitable control protocols can be selected (and possibly modified) with suitable series of pulse sequence PS as explained above.

The MRI apparatus 1 according to the disclosure, and in particular the control device 13, can have a number of additional components that are not shown in detail but are typically present at such apparatuses, for example a network interface in order to connect the entire apparatus with a network and be able to exchange raw data and/or image data or, respectively, parameter maps, but also additional data (for example patient-relevant data or control protocols).

All systems, devices and units described here that have a function in the MRT-apparatus (and are not the scanner) may be regarded as infrastructure units. Thus, infrastructure units are here the central control device 13, the sequence control unit 14, the radio-frequency transmission device 15, the gradient system interface 16, the radio-frequency reception device 17, the reconstruction unit 18 and the memory 19.

Additional infrastructure units (not shown here) are power units, cooling units, sensor units and units driving auxiliary systems.

FIG. 2 shows a simplified system 12 for medical data/image acquisition according to an aspect of the disclosure. This system 12 comprises components as already described above. In contrast to the MRI-apparatus 1 the system comprises three scanners 2 and a number of infrastructure units for the operation of the scanners 2. In this example, the control device 13 comprises an additional scheduling unit 23 and is configured as a performance scheduling device 13a together with a power unit 20 it is used as common infrastructure unit. The performance scheduling device 13a is designed such that it drives all three scanners 2 and the system is designed such that the power unit is able to apply a basic magnetic field to two scanners 2 (the third scanner may have its own power supply that is not shown).

In contrast to the performance scheduling device 13a that is in this example hardwired to the three scanner units 2 via interlinkage means 21 (here data lines and/or power lines), the power unit is not hardwired to the magnets of the scanners. The interlinkage means 21 (power lines) from the scanners 2 are able to be connected to the power unit 20 via a switch unit 22 designed to connect and disconnect a number of scanners to/from the common infrastructure unit by connecting or disconnecting interlinkage means. In the shown example, the upper scanner 2 is connected with the power unit, while the right scanner 2 is disconnected. However, the switch unit 22 can connect the right scanner 2 (or disconnect the upper scanner 2) when a common operation schedule dictates that. For this reason the switch unit has a data connection to the performance scheduling device 13a for control.

In this example, the upper scanner 2 is designed as superconducting scanner 2, having its own cooling device 24 as (individual) infrastructure unit.

FIG. 3 shows a block diagram of the process flow of a preferred method according to the disclosure e.g. for controlling a system 12 as shown in FIG. 2. In the following a system as shown in FIG. 2 with three scanners is regarded, however, the number "three" can also be read as "two or more".

In step I, operation schedules SO for the three scanners 2 are determined (e.g. from data stored in the memory 19) or provided (e.g. from a user). This operation schedules SO are the three schedules for the operation of each of the three scanners 2 and provide information when which examination procedures are applied in the next (or at least a following) time period.

In step II, a combined operation schedule SC is determined from the operation schedules SO of the three scanners 2. the combined operation schedule SC is e.g. determined in that it is first determined based on the operation schedules SO of the scanners when the scanners are used at the same time and, whether the combined performance of the scanners exceeds the technical properties of a respective common infrastructure unit at a certain period of time. Then the combined operation schedule SC can be arranged such that during combined performance two or all three scanners are driven by one single infrastructure unit, e.g. a power unit for the basic magnetic field and/or a cooling unit or even a gradient unit during a synchronized measuring procedure of the scanners.

In a time period when the combined performance of the scanners exceeds the technical properties of a respective common infrastructure unit, one or two scanners are decoupled from the respective infrastructure unit and coupled to another infrastructure unit. It is also possible that another common infrastructure unit is added to aid the first common infrastructure unit. Although peak performance could result in the costs for an additional infrastructure unit, these costs are not necessary in any case. The combined operation schedule can also shift the schedule of a scanner to times where the load is low so that no peaks occur that exceed the technical properties of a respective common infrastructure unit.

To achieve this, the need of a system for a specific infrastructure medium could be estimated with an iterative procedure. In a first time period, the system is provided with a proportional scale of infrastructure units to the number of scanners. Thus, in the first time period every scanner has its own infrastructure units. In the first time period, the maximum need of the infrastructure media is determined.

Then, after the first time period, the number of infrastructure units in respect to an infrastructure medium is reduced subsequently until the maximum need of the respective infrastructure medium is just assured. Thus, the supply of the respective infrastructure medium is covered by a smaller number of respective infrastructure units than in the first time period (at least depending from the maximum need).

In step III, the three scanners are driven combined with the common infrastructure unit at least temporally, according to the determined combined operation schedule SC. Regarding infrastructure units that have a direct effect on the measurement (e.g. gradient power supply in contrast to cooling), the scanners could be driven in a synchronized measurement procedure by a number of common infrastructure units, preferably wherein measurement protocols are scheduled that are similar in regard to the respective infrastructure medium or the time course of the change of the infrastructure medium.

Although the present disclosure has been disclosed in the form of preferred aspects and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The invention claimed is:

1. A system for medical data acquisition, comprising:
   a plurality of scanners;
   a plurality of infrastructure units configured to operate the scanners, wherein the system is configured to use at least one of the infrastructure units as a common infrastructure unit to operate at least two of the plurality of scanners; and
   a performance scheduling device configured to generate a notification when a requirement of the plurality of scanners to use an infrastructure medium provided by the common infrastructure unit during a determined time interval would exceed a capability of the common infrastructure unit to provide the infrastructure medium.

2. The system according to claim 1, wherein an infrastructure unit from among the plurality of infrastructure units is selected from the group consisting of a cooler, a sensor, an energy supply for auxiliary systems, a general power supply, a power amplifier, an image reconstruction unit, an analyzer, a user interface, a shielding, and an insulator.

3. The system according to claim 1, wherein the common infrastructure unit is a cloud system configured to provide capacity for image reconstruction, analysis, or control information for the plurality of scanners.

4. The system according to claim 1, further comprising:
an interlinkage comprising power conductors, pipes, or data lines connecting the common infrastructure unit with the plurality of scanners to provide an infrastructure medium; and
a switch configured to, selectively couple the plurality of scanners and the common infrastructure unit by connecting or disconnecting the interlinkage.

5. The system according to claim 1, further comprising:
a scheduler configured to manage a dynamic connection of the plurality of scanners to the common infrastructure unit depending on a performance of the common infrastructure unit,
wherein the common infrastructure unit is configured to provide a predefined threshold capacity of the respective infrastructure medium required by the plurality of scanners.

6. The system according to claim 1, wherein:
two or more common infrastructure units are independently connectable to and disconnectable from the same ones of the plurality of scanners,
a further common infrastructure unit is connectable with the plurality of scanners, and
the common infrastructure unit connected to the plurality of scanners is disconnectable afterwards.

7. A method for controlling a system for medical data acquisition having a plurality of scanners and a plurality of infrastructure units to operate the plurality of scanners, the system being configured to use at least one of the infrastructure units as a common infrastructure unit to operate at least two of the plurality of scanners, the method comprising:
providing or determining an operation schedule for operation of the plurality of scanners;
determining a combined operation schedule of combined operation of the plurality of scanners with a concerted use of a common infrastructure unit based on the operation schedule and technical properties of the common infrastructure unit;
operating the at least two of the plurality of scanners according to the determined combined operation schedule; and
generating a notification when a requirement of the plurality of scanners to use an infrastructure medium provided by the common infrastructure unit during a determined time interval would exceed a capability of the common infrastructure unit to provide the infrastructure medium.

8. The method according to claim 7, wherein the act of determining
the combined operation schedule comprises initially providing the system with a proportional scale of infrastructure units to a number of the plurality of scanners, and further comprising:
after a time period, reducing the number of infrastructure units with respect to an infrastructure medium when a predetermined requirement for the respective infrastructure medium during the time period is covered by a smaller number of respective infrastructure units.

9. The method according to claim 7, further comprising:
determining the combined operation schedule based on smart multiplexing or interleaving of a usage of infrastructure units for the plurality of scanners;
determining, based on the operation schedule of the plurality of scanners, whether the combined performance of the plurality of scanners exceeds a technical property of the common infrastructure unit at a predetermined period of time; and
when the combined performance of the plurality of scanners exceeds the technical property of the common infrastructure unit, disconnecting one of the plurality of scanners from the common infrastructure unit or another infrastructure unit for a respective infrastructure medium that is connected to the plurality of scanners.

10. The method according to claim 7, further comprising:
driving the plurality of scanners in a synchronized measurement procedure by a plurality of common infrastructure units; and
scheduling measurement protocols based upon a respective infrastructure medium or a change of the infrastructure medium over time.

11. The method according to claim 7,
wherein the operation schedule of at least two of the plurality of scanners corresponds to a time period longer than a month.

12. The method according to claim 7, wherein the system comprises a further infrastructure unit in addition to the common infrastructure unit, and
wherein the additional infrastructure unit is connectable to a further scanner of the system.

13. A non-transitory computer-readable medium having stored thereon program elements that, when executed by one or more processors of a performance scheduling device, cause the performance scheduling device to:
provide or determine an operation schedule for the operation of a plurality of scanners;
determine a combined operation schedule of combined operation of the plurality of scanners with a concerted use of a common infrastructure unit based on the operation schedule and technical properties of the common infrastructure unit;
operate the at least two of the scanners according to the determined combined operation schedule; and
generate a notification when a requirement of the plurality of scanners to use an infrastructure medium provided by the common infrastructure unit during a determined time interval would exceed a capability of the common infrastructure unit provide the infrastructure medium.

* * * * *